United States Patent [19]

Bontemps

[11] Patent Number: 5,707,657
[45] Date of Patent: Jan. 13, 1998

[54] FOOD SUPPLEMENT CONTAINING ANIMAL FETAL MESENCHYMAL MATTER AND ANIMAL FETAL ORGAN EXTRACTS

[76] Inventor: Raymond Bontemps, 5, avenue de la Grande Armée, 75016 Paris, France

[21] Appl. No.: 391,322

[22] Filed: Feb. 21, 1995

Related U.S. Application Data

[63] Continuation of Ser. No. 253,675, Jun. 3, 1994, abandoned, which is a continuation of Ser. No. 18,868, Feb. 17, 1993, abandoned.

[30] Foreign Application Priority Data

Feb. 18, 1992 [FR] France .................... 9201822

[51] Int. Cl.$^6$ .................... A61K 35/12; A61K 35/48; A61K 35/407; A61K 35/30
[52] U.S. Cl. .................... 424/572; 424/520; 424/553; 424/570; 424/582; 424/583; 426/531; 426/641; 426/648; 426/655
[58] Field of Search .................... 424/520, 553, 424/570, 582, 583, 572; 426/531, 641, 648, 655

[56] References Cited

U.S. PATENT DOCUMENTS

| | | | |
|---|---|---|---|
| 4,271,148 | 6/1981 | Keeling | 424/553 |
| 4,908,206 | 3/1990 | Schäfer et al. | 424/582 |
| 5,175,004 | 12/1992 | Matsumura | 424/520 |
| 5,434,341 | 7/1995 | Outzen | 800/2 |
| 5,496,722 | 3/1996 | Goodwin et al. | 435/240.23 |

FOREIGN PATENT DOCUMENTS

| | | | |
|---|---|---|---|
| 8503646 | 3/1985 | France . | |
| 1467791 | 12/1968 | Germany | 424/582 |
| 0423192 | 1/1935 | United Kingdom | 424/553 |

OTHER PUBLICATIONS

Fukamachi, H. et al., Experientia, vol. 42(3), pp. 312–315, 1986.

*Primary Examiner*—Michael G. Wityshyn
*Assistant Examiner*—Kristin K. Larson
*Attorney, Agent, or Firm*—Cummings & Lockwood

[57] ABSTRACT

A food supplement comprises isolated animal mesenchymal matter of fetal origin and extracts of animal organs of fetal origin, the mesenchymal matter consisting of a network of loose connective tissue and the food supplement being free of chemical preservatives.

3 Claims, 1 Drawing Sheet

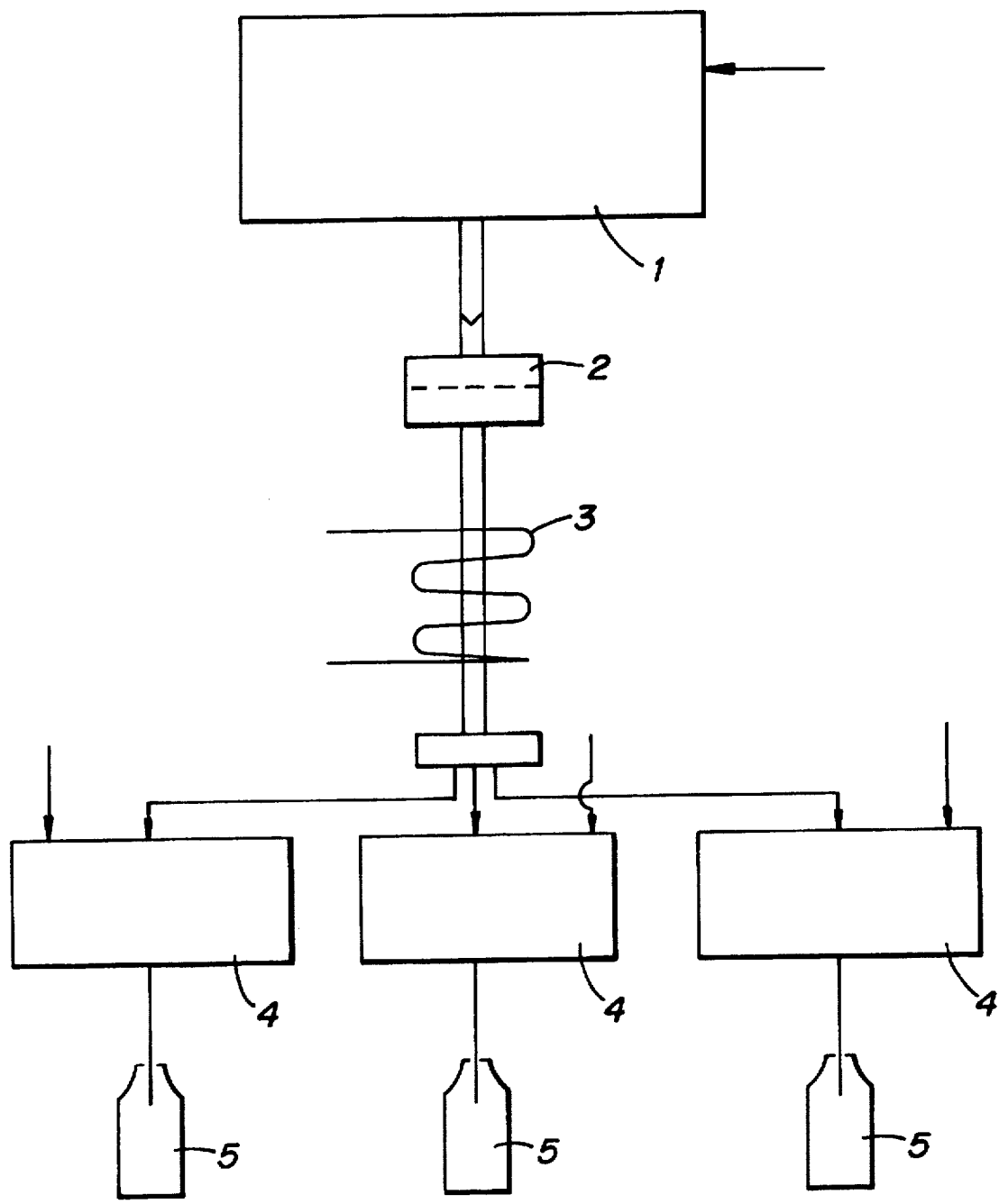

FOOD SUPPLEMENT CONTAINING ANIMAL FETAL MESENCHYMAL MATTER AND ANIMAL FETAL ORGAN EXTRACTS

This application is a continuation of application Ser. No. 08/253,675, filed Jun. 3,1994, now abandoned, which is a continuation of application Ser. No. 08/018,868, filed Feb. 17, 1993, now abandoned.

BACKGROUND ART

Until now, mesenchymous matter of fetal origin, such as the allantoic fluid, the ophthalmic extract, the Mechkel cartilage and the Wharton jelly, have been collected by means of a syringe.

The collected biogenic mesenchymous matter was supposed to contain a certain proportion of macromolecules of the ribonucleic acid type (RNA, DNA) which generate living material and natural amino acids. This collected matter which was not free of bacteria or viruses was then dissolved at room temperature in a physiological serum in order to make up a gel. In order to eliminate traces of bacteria and viruses, traces of oxoquinoline, a preservative were added. The gel was then filtered to eliminate the particles whose size was greater than 0.2μ. After this preparation, the gel was again diluted in a volume of physiological serum so as to obtain a solution containing an amount of proteins or active substances which rated when analyzed with a refractometer at e value of 12° to 15° for a preparation based on Meckel cartilage, and 20° for a preparation based on Wharton jelly.

A substance and a solution were thus obtained which were assumed to constitute one of the fundamental mesenchymous substances that create native living tissues.

SUMMARY OF THE INVENTION

The invention, the subject of this patent, concerns a process for the preparation of a food supplement obtained from a device capable of providing mesenchymous matter comprising, particularly natural amino acids. This mesenchymous matter which is particularly susceptible to deterioration, is filtered, frozen, ground in an aseptic chamber, and mixed with physiological serum, to be ultimately used in the preparation of particularly active food supplements.

BRIEF DESCRIPTION OF THE DRAWINGS

FIG. 1 represents a schematic diagram of the various elements of the apparatus used to carry out the process of the present invention.

According to FIG. 1, the principle of the process is characterized by a tank (1) containing fresh mesenchymous matter stored at low temperature which is filtered on micropores or sieves (2), frozen and then grinded, diluted in physiological serum (4) and mixed with food. The mesenchymous substances resulting from this process constitute an active food supplement. The invention is used in the food industry and dietetics.

DETAILED DESCRIPTION OF THE INVENTION

Mesenchymous matter is of fetal origin and has a biogenic character. Mesenchymous substances obtained from the process of the invention contain amino acids whose chemical bonds are unsaturated. Mesenchymous substances constitute particularly active microseptors to the extent that some of their chemical bonds contain free radicals which easily attach to tissues of living organs. This binding originates from free electrical bonds which catalyze rapid absorption and facilitate assimilation of the mesenchymous substances by the diseased or fatigued organs of an individual.

Moreover, natural amino acids are particularly appreciated for their regenerating and stimulating effects. Their activity is important because the fresh mesenchymous matter is extracted and absorbed under conditions that are such that these mesenchymous substances are not altered over time. The use of low conservation temperatures, in the neighborhood of $-20°$ C., results in their initial properties (being kept intact and solves the previous problems of preservation.

The faculty of regeneration of mesenchymous substances is explained by the fact that these substances are composed of nonpolymerized macromolecules, mixed with native amino acids endowed with an inductive electrical memory and capable of being base elements for the regeneration of living tissues. These substances can be selectively absorbed onto certain tissues to constitute memory microseptors.

It has also been found that mesenchymous matter which mainly consists of a native network of loose connective tissue, also comprises, between the network of loose connective tissues; a fundamental mucous substance having as basic components proteins constituting memory microseptors.

Depending on the origin of the embryonic mesenchymous matter, the proportions of native connective tissues, proteins, amino acids, or simple DNA or RNA molecules vary.

For example, in the case of Wharton jelly, the extra-embryonic mesenchymous substance represents a reticular magma of the blastocel and makes up a fetal substance particularly rich in proteins which overlays a diseased native connective tissue.

Meckel cartilage is a mesenchymous matter of fetal origin which contains collagen fibers or polymerized proteins and numerous elastic fibers having a connective character, which can be used in dermatology.

When the evolution of these fetal substances is studied over time, a transformation either into muscular fibers or into connective tissues capable of regenerating the skin or specific organ of an individual is observed. These substances are used as microseptors because they progressively form a blood circulation and an electrical nerve network comprising pseudo-neurons which provide real sensory programming from which their use as a microseptor is derived.

It was also observed that these mesenchymous substances are capable of repairing tissues of an organ which have been subjected to a particularly profound attack, whereby the regenerating capacity of this organ has been partially destroyed. It was therefore observed that these mesenchymous substances have the capacity to provide to the living organism means for its regeneration through the primary and polarized elements that they contain which are called microseptors.

However, these mesenchymous substances are only particularly active when they are fresh and introduced into the organism in their initial state. Moreover, the presence of preservatives destroys the catalytic effect of the essential elements of the mesenchymous substances. In order to introduce these substances into the organism under the best efficacy conditions, they are combined with extracts of specific organs.

In order to make the food supplement according to the invention, the following method is used:

in situ removal of mesenchymous matter and extracts from specific organs (liver, brain. etc.), under absolute aseptic conditions, freezing and preservation of the removal mesenchymous substances in the absence of a preservative, purification by filtration and dilution in a sealed aseptic chamber.

The present invention, called: <<Process for preparation of food supplements based on mesenchymous substances of the microseptor type>>, is characterized by the following steps. The removal of mesenchymous substances from living matter or matter considered as such is carried out in an aseptic chamber. The sample comprises mesenchymous substances containing natural amino acids, into which are added organ extracts of fetal origin (liver, brain, etc.) or substances used to feed a fetus (animal or other). The sample is then maintained at a temperature of −20° C. in an aseptic container. Physiological serum is added to the frozen sample so as to transform it into magma. The magma is filtered on a micropore filter or sieve whose pore openings are less than 0.2μ in order to eliminate particles of a size larger than 0.2μ. This filtration also eliminates certain bacteria and viruses. The temperature of the magma is then brought back to −20° C. in order to solidify it. The solid magma is then cold ground and mixed with physiological serum to obtain a clear solution constituting an active food supplement. The activity of the food supplement is varied by controlling dilution of the mixture with physiological saline on the food supplement solidified at −20° C. and powered at this temperature.

The preparation process for these food supplements will be better understood by means of several examples of manufacture described by means of FIG. 1, which is a synoptic diagram representing the cycles of the process.

The extraction and drying of mesenchymous substances such as ophthalmic extract or allantoidian fluid are carried out under absolute sterilization conditions.

These different substances are associated with amino acids of fetal origin which preside in the creation of a fetus.

According to their origin (allantoidian or ophthalmic) these substances are extracted, mixed and stored in a container (1) immediately after their extraction. This container is kept at the temperature of −20° C. These temperature conditions are required in order to destroy any microbial proliferation. To the mesenchymous substances collected are added a small volume of physiological serum in order to obtain a gelatinous magma. In order to eliminate certain cells or bacteria, this gel is filtered under pressure or by suction through a micropore filter (2) capable or retaining the particles and viruses having a size greater than 0.21μ. Filtration of this mixture is carried out at a temperature close to 0° C. at level (2), in order to increase the solubility of the mesenchymous substances and of the extracts of vital organs of fetal origin (liver, brain, etc.) in the small volume of physiological serum. Immediately after filtration, this mixture is brought back to a temperature of −20° C. at level (3) by means of cooling coils.

At level (3) a solid is obtained which can be ground at −20° C. This grinding allows homogenization of the mixture and obtaining of a powder. Depending on the origin of the extracted mesenchymous substances and on the organ extracts introduced (liver, brain), generally of fetal origin, the powders obtained are treated in separate circuits placed in parallel and in an identical manner with respect to the steps of the process. This allows to obtain food supplements with different and specific activities.

These powders are kept at −20° C. and will be diluted by a volume of physiological serum (4) until a clear liquid is obtained, which is stored at a temperature of −20° C. in sealed bottles (5) whose volume corresponds to a useful dose, and kept in an septic atmosphere. Each bottle constitutes a food-supplement treatment specific to an individual.

I claim:

1. A food supplement comprising isolate animal mesenchymal matter of fetal origin and extracts of animal organs of fetal origin, said mesenchymal matter consisting of a network of loose connective tissue and said food supplement being free chemical preservatives.

2. The food supplement according to claim 1, wherein said organ extracts of fetal origin are liver and brain extracts.

3. The food supplement of claim 1 wherein said mesenchymal matter is selected from the group consisting of Meckel cartilage and Wharton jelly.

* * * * *

UNITED STATES PATENT AND TRADEMARK OFFICE
CERTIFICATE OF CORRECTION

PATENT NO. : 5,707,657
DATED : January 13, 1998
INVENTOR(S) : Raymond Bontemps

It is certified that error appears in the above-identified patent and that said Letters Patent is hereby corrected as shown below:

Claim 1, column 4, line 31, delete "isolate"
and insert --isolated-- therein.

Claim 1, column 4, line 35, after the word "free"
insert --of--.

Signed and Sealed this

Tenth Day of March, 1998

Attest:

BRUCE LEHMAN

Attesting Officer

Commissioner of Patents and Trademarks